US012576499B2

(12) United States Patent
Stroh

(10) Patent No.: US 12,576,499 B2
(45) Date of Patent: Mar. 17, 2026

(54) POWER ADAPTER FOR A POWERED TOOL

(71) Applicant: Shukla Medical, St. Petersburg, FL (US)

(72) Inventor: Austin Ryan Stroh, Lutz, FL (US)

(73) Assignee: Shukla Medical, St. Petersburg, FL (US)

( * ) Notice: Subject to any disclaimer, the term of this patent is extended or adjusted under 35 U.S.C. 154(b) by 0 days.

(21) Appl. No.: 18/160,026

(22) Filed: Jan. 26, 2023

(65) Prior Publication Data

US 2023/0234202 A1 Jul. 27, 2023

Related U.S. Application Data

(60) Provisional application No. 63/303,563, filed on Jan. 27, 2022.

(51) Int. Cl.
*A61B 17/16* (2006.01)
*B25F 3/00* (2006.01)
*A61B 17/00* (2006.01)

(52) U.S. Cl.
CPC .............. *B25F 3/00* (2013.01); *A61B 17/162* (2013.01); *A61B 2017/00486* (2013.01)

(58) Field of Classification Search
CPC ... B25C 1/06; B25C 1/047; B25F 3/00; A61B 17/162; A61B 2017/00486; A61B 17/1622
USPC ........ 173/197, 81, 90, 140–141, 162.1, 213, 173/168–171
See application file for complete search history.

(56) References Cited

U.S. PATENT DOCUMENTS

| | | | | |
|---|---|---|---|---|
| 4,818,157 A | * | 4/1989 | Kouvelis .............. | B25D 17/005 81/125 |
| 5,398,946 A | * | 3/1995 | Quiring ................ | B25D 17/088 403/325 |
| 5,576,501 A | * | 11/1996 | Huang .................. | B25B 13/463 81/473 |
| 6,311,786 B1 | * | 11/2001 | Giardino ............. | B25B 23/1405 173/183 |
| 7,004,668 B2 | * | 2/2006 | Lombardo ................ | F16C 1/08 403/333 |
| 7,637,327 B2 | * | 12/2009 | Grunig ................. | B25D 17/005 173/90 |
| 8,109,183 B2 | * | 2/2012 | Santamarina ....... | B25B 23/1405 81/477 |
| 11,701,760 B2 | * | 7/2023 | Ji .......................... | B25B 21/007 81/54 |
| 2003/0098167 A1 | * | 5/2003 | Giardino ............. | B25B 23/1405 173/176 |

(Continued)

FOREIGN PATENT DOCUMENTS

| | | | | | |
|---|---|---|---|---|---|
| DE | 4330728 A1 | * | 3/1995 | ........... | B23B 45/003 |
| GB | 2174934 A | * | 11/1986 | ........... | B25D 17/088 |

(Continued)

*Primary Examiner* — Robert F Long

(74) *Attorney, Agent, or Firm* — Kim IP Law Group LLC

(57) ABSTRACT

A power adapter includes an adapter shaft having a first end for coupling to a rotary tool and a second end configured to be coupled to a working tool. Additionally, the second end includes a slot. The power adapter also includes a locking mechanism operatively coupled to the second end of the adapter shaft. The locking mechanism includes a dowel pin movable between a first position and a second position within the slot.

13 Claims, 11 Drawing Sheets

(56)                    References Cited

U.S. PATENT DOCUMENTS

| | | | | |
|---|---|---|---|---|
| 2004/0231869 A1* | 11/2004 | Bernhart | ............... | B25D 17/06 |
| | | | | 173/210 |
| 2005/0016333 A1* | 1/2005 | Compton | ........... | B23B 31/1071 |
| | | | | 81/177.85 |
| 2005/0025592 A1* | 2/2005 | Cantlon | ............. | B23B 51/0473 |
| | | | | 408/204 |
| 2005/0135890 A1* | 6/2005 | Bauman | ................. | B23B 51/12 |
| | | | | 408/239 R |
| 2006/0175773 A1* | 8/2006 | Tsai | ......................... | B25F 3/00 |
| | | | | 279/143 |
| 2010/0282485 A1* | 11/2010 | Puzio | ................. | B25B 23/0035 |
| | | | | 173/171 |
| 2011/0036212 A1* | 2/2011 | Santamarina | .......... | B25B 23/14 |
| | | | | 81/436 |
| 2011/0186316 A1* | 8/2011 | Barhitte | .................... | B25F 5/00 |
| | | | | 173/29 |
| 2013/0245629 A1* | 9/2013 | Xie | .................... | A61B 17/1624 |
| | | | | 606/80 |
| 2015/0042052 A1* | 2/2015 | Furusawa | ............... | B23B 31/10 |
| | | | | 279/141 |
| 2018/0354104 A1* | 12/2018 | Su | ........................ | B25B 23/0035 |
| 2020/0016733 A1* | 1/2020 | Furusawa | ................. | B25F 5/02 |
| 2020/0230795 A1* | 7/2020 | Carlson | ................... | B25C 1/047 |
| 2021/0023629 A1* | 1/2021 | Kawai | .................... | B25B 21/02 |
| 2021/0129308 A1* | 5/2021 | Lee | ........................ | B25D 17/02 |
| 2022/0031346 A1* | 2/2022 | Parks | ............... | A61B 17/00234 |
| 2023/0166388 A1* | 6/2023 | Wueste | .................. | B25B 21/00 |
| | | | | 81/52 |
| 2023/0191567 A1* | 6/2023 | Opsitos, Jr. | ........... | B25B 21/023 |
| | | | | 81/464 |
| 2023/0202017 A1* | 6/2023 | Sabic | ........................ | B25F 3/00 |
| | | | | 173/217 |

FOREIGN PATENT DOCUMENTS

| | | | | |
|---|---|---|---|---|
| JP | 4607134 B2 * | 1/2011 | | |
| WO | WO-2014040980 A1 * | 3/2014 | ........... | B25D 17/088 |

* cited by examiner

36

38

POWER ADAPTER FOR A POWERED TOOL

CROSS-REFERENCE TO RELATED APPLICATIONS

This application claims the benefit of U.S. Provisional Application No. 63/303,563, filed Jan. 27, 2022, the entire disclosure of which is incorporated by reference herein in its entirety.

BACKGROUND

The subject disclosure relates generally to the field of orthopedic surgical instruments. In particular, the subject disclosure relates to a power adapter for a surgical instrument.

Rotary tools are often used to provide rotational motion to a working tool such as a surgical driver tool or other surgical instruments or accessories. However, often various working tools are needed during a single operation. Using separate rotary tools for each working tool can be expensive and time consuming in the operating room.

Thus, there is a need for a power adapter that can easily attach to and de-attach from various surgical instruments to provide power to a variety of surgical instruments or accessories. Such a need is satisfied by the power adapter of the subject disclosure.

BRIEF SUMMARY OF THE DISCLOSURE

In accordance with one example, a power adapter includes an adapter shaft having a first end for coupling to a rotary tool and a second end configured to be coupled to a working tool. Additionally, the second end includes a slot. The power adapter also includes a locking mechanism operatively coupled to the second end of the adapter shaft. The locking mechanism includes a dowel pin movable between a first position and a second position within the slot.

In accordance with one example, a power adapter includes an adapter shaft having a first end for coupling to a rotary tool and a second end configured to be coupled to a working tool. The second end includes a slot having a longitudinal axis angled relative to a longitudinal axis of the adapter shaft. The adapter shaft further includes a counterbore about its second end. Additionally, the slot is in fluid communication with the counterbore. The power adapter also includes a locking mechanism operatively coupled to the second end of the adapter shaft. The locking mechanism includes a dowel pin movable between a first position and a second position within the slot. The power adapter also includes a sliding grip configured to house the adapter shaft. The sliding grip is movable between a distal position enabling the dowel pin to assume the first position, and a proximal position enabling the dowel pin to assume the second position.

In some examples, the slot includes a longitudinal axis angled relative to a longitudinal axis of the adapter shaft.

In some examples, the adapter shaft includes a bore about its second end coaxial with a longitudinal axis of the adapter shaft.

In some examples, the adapter shaft includes a counterbore about its second end and wherein the slot is in communication with the counterbore.

In some examples, the power adapter also includes a sliding grip housing the adapter shaft.

In some examples, the sliding grip is movable relative to the adapter shaft.

In some examples, the sliding grip is movable between a proximal position enabling the dowel pin to assume the second position, and a distal position enabling the dowel pin to assume the first position.

In some examples, the locking mechanism further comprises a bushing disposed between the sliding grip and the annular shaft.

In some examples, the locking mechanism further comprises a bushing circumscribing the adapter shaft.

In some examples, the locking mechanism further comprises a bushing sliding along the adapter shaft.

In some examples, the locking mechanism further comprises a biasing member biasing the bushing into contact with the dowel pin.

In some examples, the locking mechanism further comprises a biasing member biasing the dowel pin distally towards the second end of the adapter shaft.

In some examples, the sliding grip includes an annular abutment configured to engage the bushing.

In some examples, the sliding grip includes a radially inwardly extending annular abutment adjacent the slot of the adapter shaft.

In some examples, the first end is configured as a quick connection.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purposes of illustration, there are shown in the drawings exemplary embodiments. It should be understood, however, that the subject disclosure is not limited to the precise arrangements and instrumentalities shown.

In the drawings.

DETAILED DESCRIPTION OF THE DISCLOSURE

Figures 1, 2:
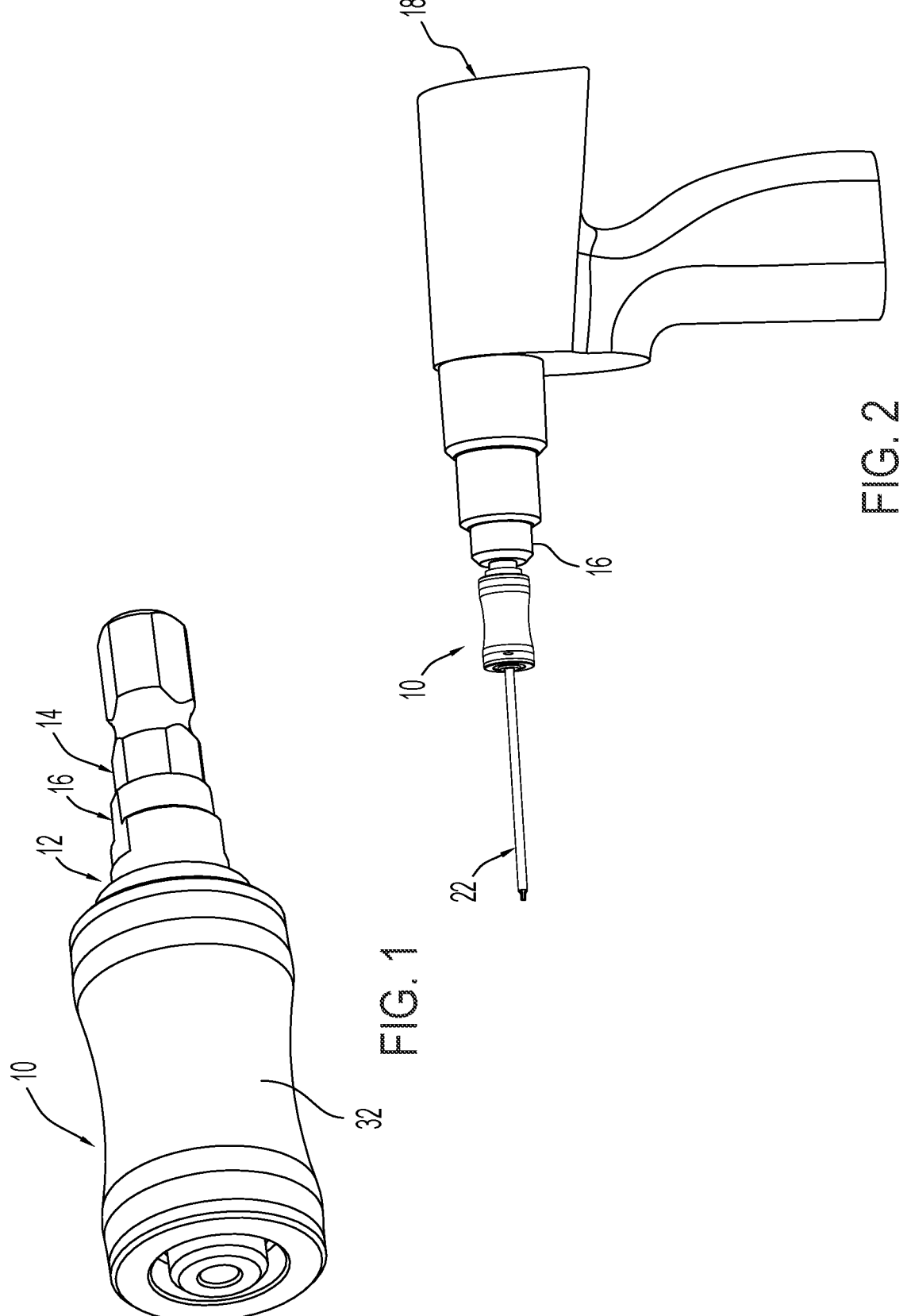
FIG. 1 is a perspective view of a power adapter in accordance with one example of the subject disclosure.
FIG. 2 is a perspective view of the power adapter of FIG. 1 coupled to a working tool and to a rotary tool.
Figure 3:
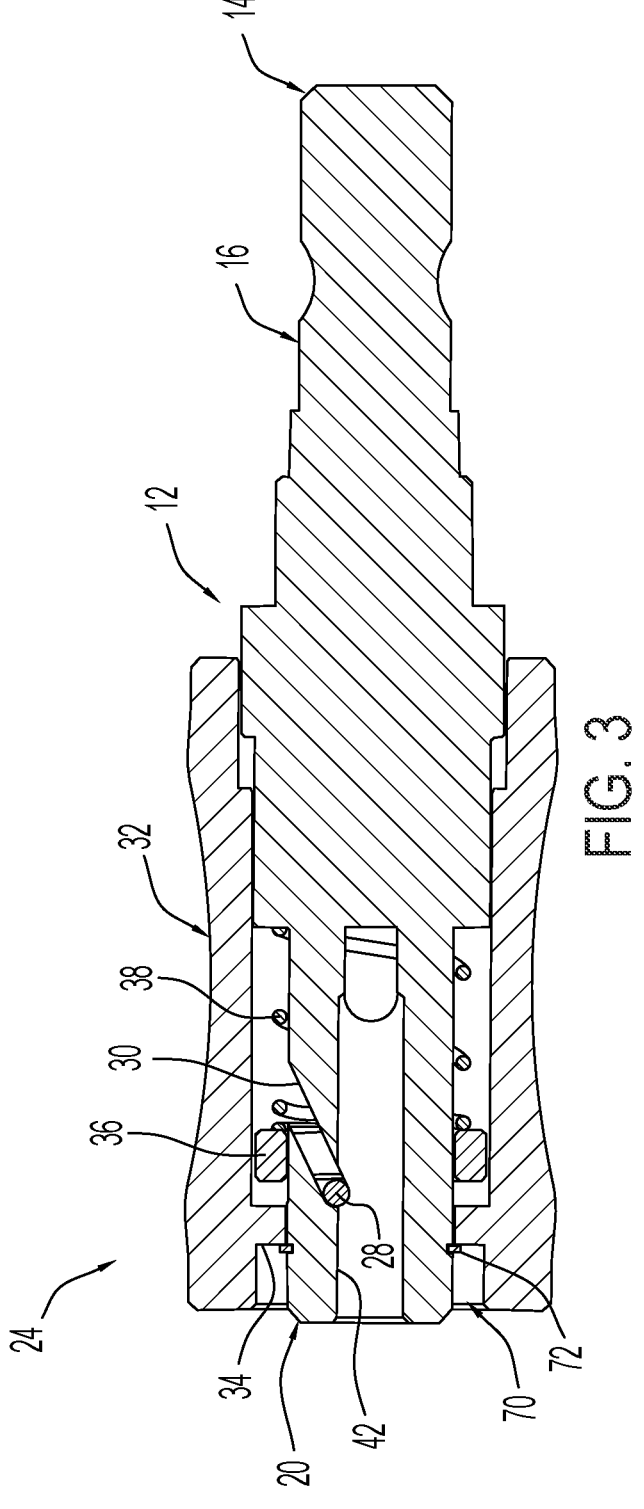
FIG. 3 is a cross-sectional view of the power adapter of FIG. 1.
Figure 4:
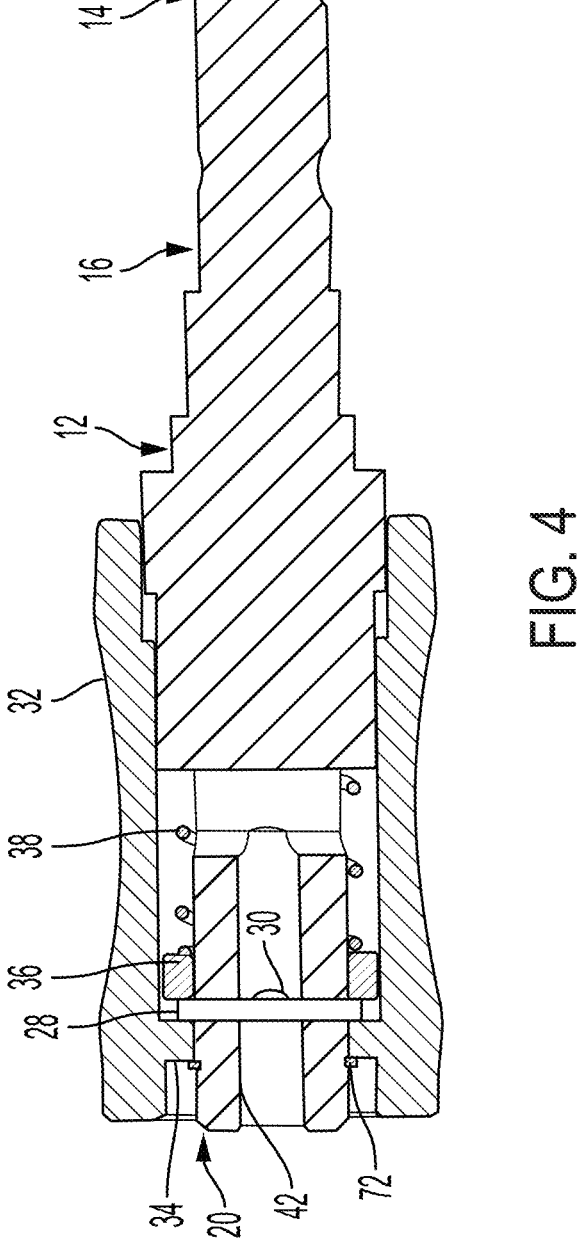
FIG. 4 is another cross-sectional view of the power adapter of FIG. 1

Reference will now be made in detail to the various examples of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, left, right, above, below and diagonal, are used with respect to the accompanying drawings. Such directional terms used in conjunction with the following description of the drawings should not be construed to limit the scope of the subject disclosure in any manner not explicitly set forth.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the identified element and designated parts thereof. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various examples of the subject disclosure can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the examples of the subject disclosure may be combined in any suitable manner in one or more examples. One skilled in the relevant art will recognize, in light of the description herein, that the subject disclosure can be practiced without one or more of the specific features or advantages of a particular example. In other instances, additional features and advantages may be recognized in certain examples that may not be present in all examples of the subject disclosure.

As shown in FIGS. 1-14, there is provided a power adapter 10 which includes an adapter shaft 12 having a first end 14 for coupling to a rotary tool 18 and a second end 20 configured to be coupled to a working tool 22, wherein the second end includes a slot 30. The power adapter 10 also includes a locking mechanism 24 operatively coupled to the second end of the adapter shaft, wherein the locking mechanism includes a dowel pin 28 movable between a first position and a second position within the slot.

In some examples, the first end 14 of the adapter shaft 12 may be configured as a quick connection for coupling to a chuck 16, such as a Jacob's chuck, of the rotary tool, however various other coupling methods are contemplated to be within the scope of the subject disclosure. In some examples, the rotary tool 18 may include, but is not limited to, a powered drill, a powered saw, or a powered reamer. However, various other tools may also be used with the described power adapter 10. In some examples, the adapter shaft 12 includes a bore 42 about its second end 20 coaxial with a longitudinal axis (A) of the adapter shaft. The bore 42, e.g., a counterbore, is operable to couple the second end 20 of the adapter shaft 12 and the working tool 22. Additionally, in some examples, a shaft of the working tool 22 configured to be coupled to the power adapter 10 includes one or more annular grooves 26 which receive the dowel pin 28 for coupling the second end 20 of the adapter shaft 12 and the working tool 22, as described in greater detail hereinafter. The working tool 22 may include but is not limited to a surgical driver tool, e.g., a surgical drill bit, a surgical screw or a surgical nut engaging bit, or the like. Additionally, the working tool 22 may be any tool whereby the rotary tool 18 may impart movement to the working tool 22.

Figure 8:
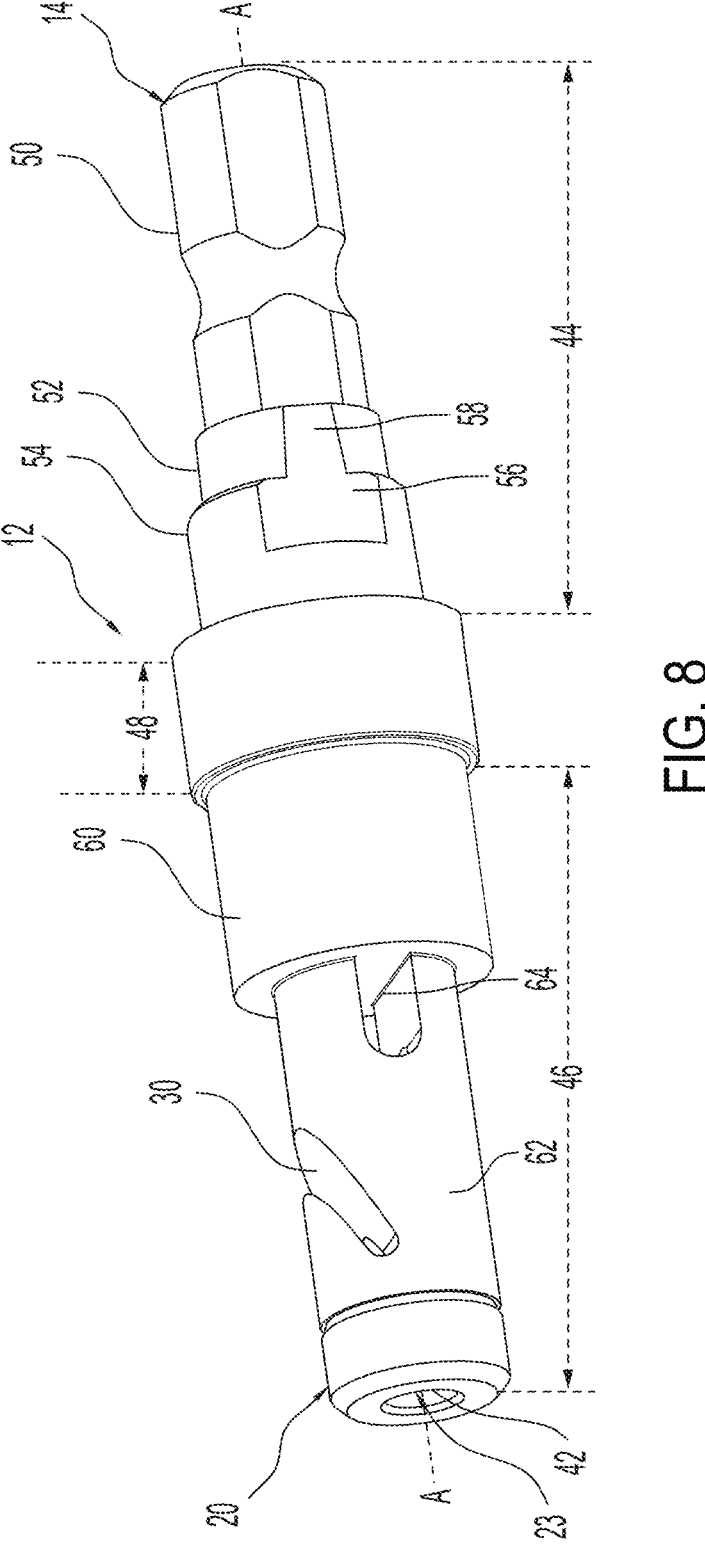
FIG. 8 is a perspective view of an adapter shaft of the power adapter of FIG. 1.
Figure 9:
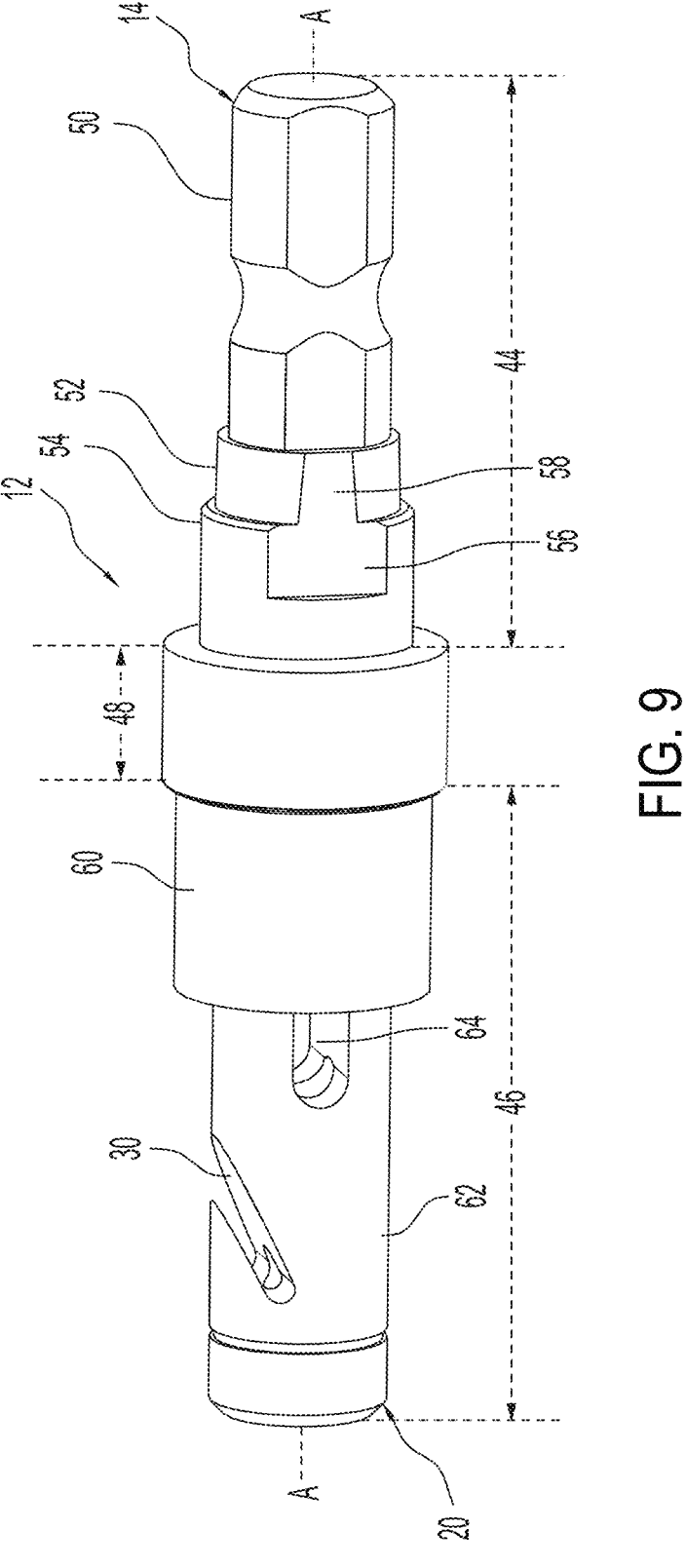
FIG. 9 is another perspective view of the adapter shaft of the power adapter of FIG. 1.
Figure 10A:
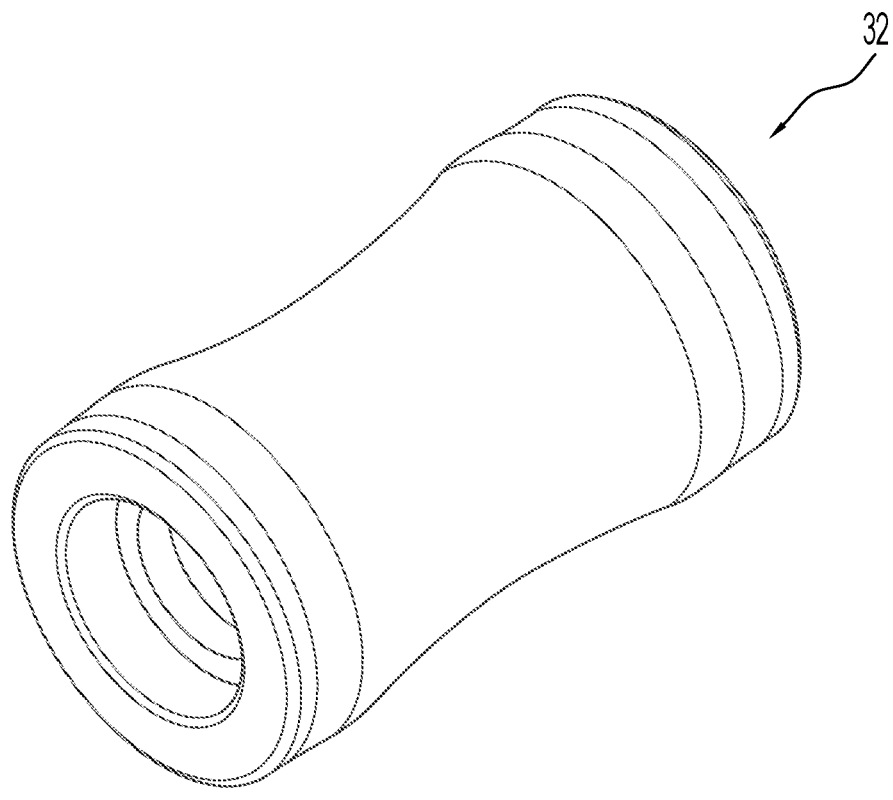
FIG. 10A is a perspective view of an exemplary sliding grip of the power adapter of FIG. 1.
Figure 10B:
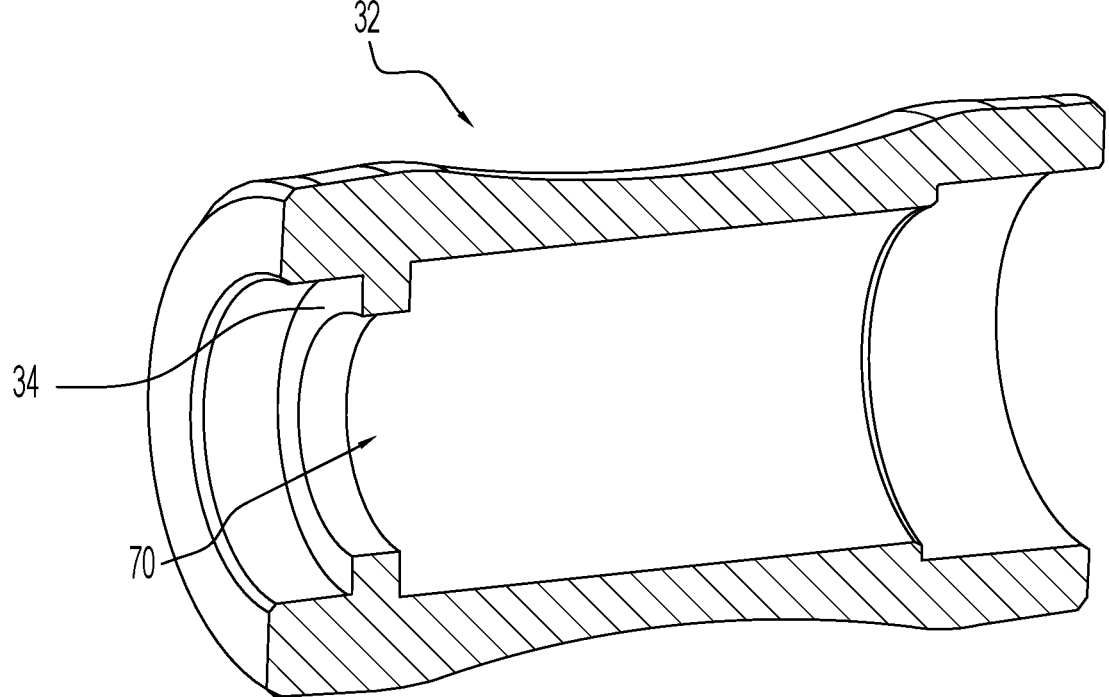
FIG. 10B is a cross-sectional view of the exemplary sliding grip of the power adapter of FIG. 10A.

As best shown in the example illustrated in FIGS. 8 and 9, the adapter shaft 12 is comprised of a plurality of portions. A first portion 44 includes the first end 14 which is configured for coupling to the rotary tool 18. A second portion 46 is disposed opposite of the first portion 44 and includes the second end 20 which is configured for coupling to the working tool 22. Moreover, the second portion 46 is configured to be coupled to the sliding grip 32. A third portion 48 is disposed between the first portion 44 and the second portion 46 and is configured to be disposed between the first end 14 and the second end 20 and disposed between the rotary tool 18 and the working tool 22.

Referring still to the example shown in FIGS. 8 and 9, the first portion 44 may be adapted for a Hudson connection or may be any other shape and size. In the example shown, the first portion 44 includes a series of cylinders disposed end to end and co-axially aligned having diminishing diameters from the proximal end of the first portion 44 to the distal end of the first portion 44. In the example shown, this series of cylinders are described as a first cylinder 50, a second cylinder 52, and a third cylinder 54 from most distal to most proximal in location along the adapter shaft 12. In the example shown, the first cylinder 50 has the longest length of the series of cylinders and has an outer surface which includes one or more substantially flat portions. One or more of the substantially flat portions are configured to engage the rotary tool 18 and the substantially flat portions prevent rotation between the rotary tool 18 and the adapter shaft 12 which allows translation of rotational force from the rotary tool 18 to the working tool 22. In the example shown, the first cylinder 50 also includes a recessed collar having a smaller diameter than the remainder of the first cylinder 50. The recessed collar is configured to engage a push to connect mechanism to secure the rotary tool 18 and the power adapter 10 in an axial direction and prevents axial movement between the rotary tool 18 and the power adapter 10 thereby allowing axial force to be translated between the rotary tool 18 and the power adapter 10.

Referring still to the example shown, the third cylinder 54 of the first portion 44 has the largest diameter of the series of cylinders and also defines at least one substantially flat portion 56. As illustrated in the example shown in FIG. 8, the substantially flat portion 56 is configured to engage a portion of the rotary tool 18 and may be rectangular in shape, as shown, or may be another shape, as desired. In the example shown, the third cylinder 54 of the first portion 44 of the adapter shaft 12 includes two cut-outs disposed opposite of one another about the first portion 44, however, various other quantities and arrangements of cut-outs are contemplated to be within the scope of the subject disclosure.

Referring still to the example shown in FIGS. 8 and 9, the second cylinder 52 has a diameter that is larger than the first cylinder 50 and smaller than the third cylinder 54. In the example shown, the second cylinder 52 also includes a substantially flat portion 58 configured to engage a portion of the rotary tool 18 and having a generally tapered shape. In some examples, the substantially flat portion 58 on the second cylinder 52 aligns with the substantially flat portion 56 on the third cylinder 54. In the example shown, the second cylinder 52 has two cut-outs 58 disposed opposite of one another about the cylinder and aligned with the substantially flat portions 56 of the second cylinder 52, however, various other quantities and arrangements of cut-outs are contemplated to be within the scope of the subject disclosure. The cut-outs 58, similar to the cut-outs 56 as described above are also configured to assist in securing the first end 14 of the adapter shaft 12 and the rotary tool 18 and to prevent axial and rotational movement therebetween. Other variations of attachment methods have also been contemplated including but not limited to other mechanical coupling methods.

The second portion 46 of the adapter shaft 12 which includes the second end 20 includes a solid cylindrical portion 60 and a bored cylindrical portion 62. The solid cylindrical portion 60 is disposed most proximally and adjacent the third portion 48. The bored cylindrical portion 62 includes the counterbore 42 coaxial with a longitudinal axis of the adapter shaft (A) configured to house a shaft 21 of the working tool 22. In some examples, the shaft 21 of the working tool 22 extends to and may abut the solid cylindrical portion 60. Additionally, the bored cylindrical portion 62 includes an aperture 64 defined adjacent to the solid cylindrical portion 60. The aperture 64 may accommodate various end geometries of the working tool 22. The aperture 64 may be generally rectangular having a rounded distal end, as shown in FIG. 8, however, various other aperture 64 shapes are contemplated to be within the scope of the subject disclosure. Moreover, the bored cylindrical portion 62 of second end 20 of the adapter shaft 12 defines a slot 30. Referring still to the example shown in FIG. 8, the slot 30 is an angled relative to the longitudinal axis (A) of the adapter shaft 12. In the example shown, the slot 30 has a relative angle of approximately 40-50 degrees. However, it is also contemplated that the slot 30 may be at another relative angle including but not limited to 30-60 degrees, 20-70 degrees, 10-80 degrees, or 5-90 degrees. In some examples, such as in the example shown in FIG. 3, the slot 30 has a length such that the slot 30 is in communication with the counterbore 42 of the second end 20 of the adapter shaft 12 which allows for coupling of the working tool 22 and the second end 20 of the adapter shaft 12, as explained in more detail below. Additionally, the bored cylindrical portion 62 includes a sliding collar 72 disposed adjacent the second end of the adapter shaft. In the example shown, the sliding collar 72 is annular such that it circumscribes the adapter shaft. Moreover, the sliding collar 72 may be another shape or size as desired.

Referring still to the example shown in FIGS. 1-14, the power adapter 10 also includes the sliding grip 32. The sliding grip 32 is generally cylindrical in shape and is configured to be disposed around the second end 20 of the adapter shaft 12. In other words, the sliding grip 32 is configured to at least partially house the second end 20 of the adapter shaft 12. Moreover, in the example shown, the sliding grip 32 includes substantially the same diameter at its distal and proximal ends. Additionally in the example shown, the sliding grip 32 includes a tapered middle portion having a smaller diameter than the remainder of the second portion 46. The middle portion may be adapted to allow a user to easily engage with the sliding grip 32 to releasably secure the power adapter 10 to the working tool 22. However, it is also contemplated that the sliding grip 32 maintains the same diameter along its length such that the sliding grip 32 does not include a tapered middle portion. In some examples, the sliding grip 32 may be comprised of stainless steel or other metal similar to the other components of the power adapter 10. However, it is also contemplated that the sliding grip 32 may include an outer surface which assists a user in gripping and moving the sliding grip 32 between the distal position and the proximal position.

Figure 5:
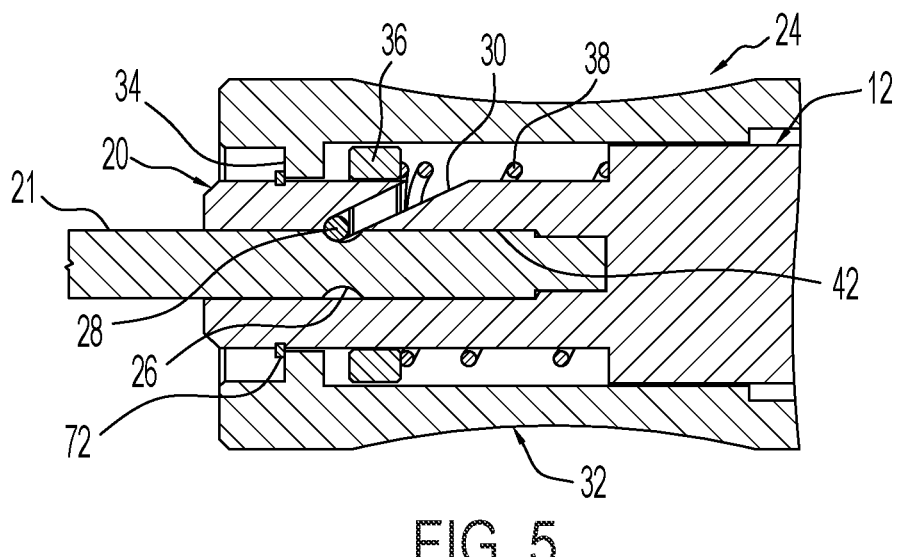
FIG. 5 is a partial cross-sectional view of the power adapter of FIG. 1 having the working tool coupled thereto.
Figure 7:
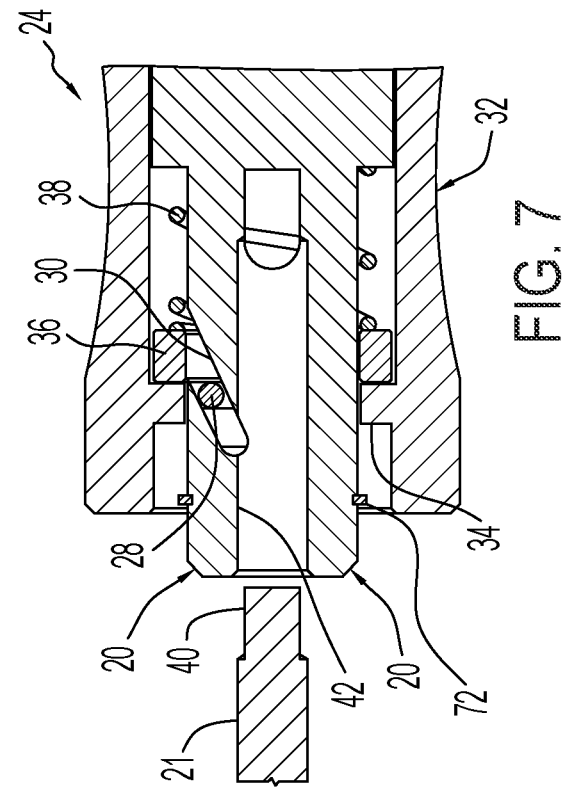
FIG. 7 is a partial cross-sectional view of the power adapter of FIG. 1 having the working tool uncoupled from the power adapter.
Figure 6:
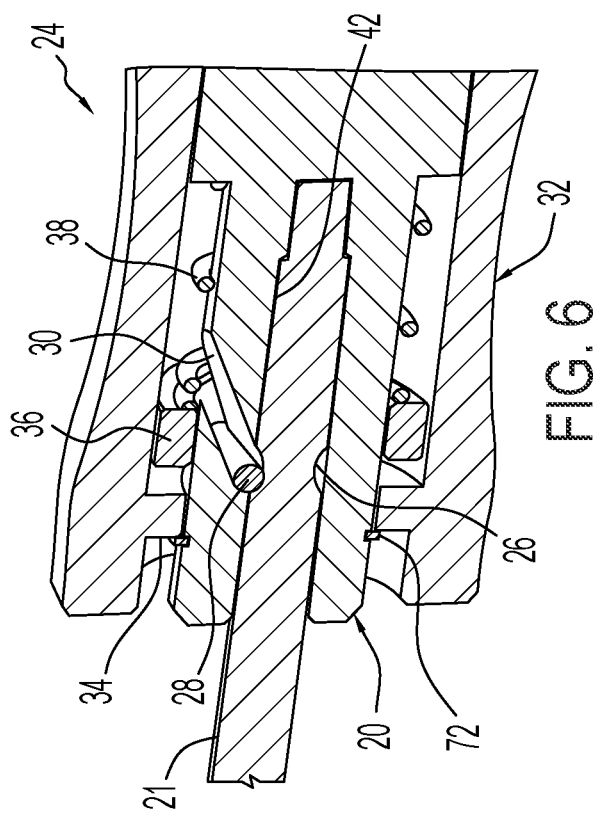
FIG. 6 is a perspective view of the partial cross-sectional view of the power adapter shown in FIG. 5.

The sliding grip also defines a bore 70 at least partially therethrough to allow the second end 20 of the adapter shaft 12 to be disposed therethrough. As best illustrated in FIGS. 3-7, the second end 20 of the adapter shaft 12 extends all the way through the bore 70 of the sliding grip 32 such that a user may easily couple the working tool 22 with the second end 20 of the adapter shaft 12 without interference from the sliding grip 32. However, various other configurations are contemplated to be within the scope of the subject disclosure. In the example shown, the bore 70 of the sliding grip 32 is disposed co-axial with the counterbore 42 of the adapter shaft 12, however, various other configurations are contemplated to be within the scope of the subject disclosure. In some examples, the sliding grip 32 is movable relative to the adapter shaft 12. More specifically, in some examples, the sliding grip 32 is movable between a distal position where the sliding grip 32 is disposed closer to the second end 20 of the adapter shaft 12 and a proximal position where the sliding grip 32 is disposed further from the second end 20 of the adapter shaft 12. In some examples, the sliding grip 32 also includes an annular abutment 34 disposed on its inner surface. Additionally, in some examples, the annular abutment 34 is a radially inwardly extending annular abutment 34 disposed adjacent the slot 30 of the adapter shaft 12. However, various other configurations of abutments are contemplated to be within the scope of the subject disclosure. Moreover, the annular abutment 34 is movable with the sliding grip 32 between the distal position and the proximal position. As illustrated in FIGS. 5 and 6, when the sliding grip is in the distal position, the annular abutment 34 is disposed against the collar 72 of the second portion 46 of the adapter shaft 12. As shown in FIG. 7 and as described in greater detail below, when the sliding grip 32 is moved towards the proximal position, the annular abutment 34 moves correspondingly and engages and moves a bushing 36 of the locking mechanism 24 against the bias of a biasing member 38 to allow the dowel pin 28 to freely move proximally in slot 30 towards a first or proximal position out of engagement with the working tool 22.

Referring again to the example shown in FIGS. 8 and 9, the third portion 48 of the adapter shaft 12 is disposed between the first portion 44 and the second portion 46. In the example shown, the third portion 48 is a generally smooth cylinder having the same diameter along its length. Moreover, the third portion 48 of the adapter shaft 12 has a greater diameter than the first and second portion 46s but a smaller diameter than the sliding grip 32. Additionally, it is contemplated that the third portion 48 may include cut-outs, protrusions, or other engagement features, if desired.

The power adapter 10 further includes the locking mechanism 24 operatively coupled to the second end 20 of the adapter shaft 12. The locking mechanism 24 includes a dowel pin 28 movable between a first position and a second position within the slot 30. In the first position, the dowel pin 28 is disposed partially seated in both the slot 30 and the counterbore 42 and the dowel pin 28 is configured to engage the shaft of the working tool 22. In the second position, the dowel pin 28 is moved proximally and away from the counterbore 42 such that the dowel pin 28 is completely seated within the slot 30 and disposed away from the counterbore 42, allowing the shaft of the working tool 22 to be released from the counterbore 42.

Figure 11:
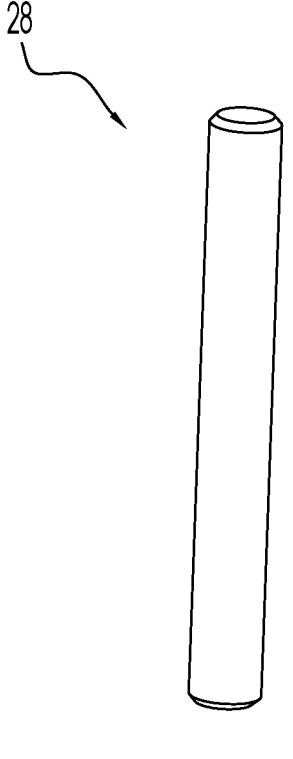
FIG. 11 is a perspective view of a dowel pin of the power adapter of FIG. 1.
Figure 12:
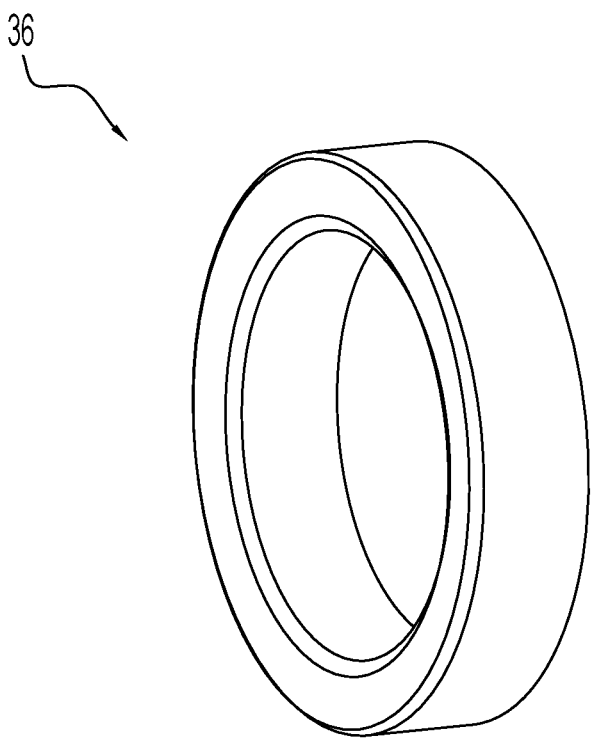
FIG. 12 is a perspective view of a bushing of the power adapter of FIG. 1.
Figure 13:
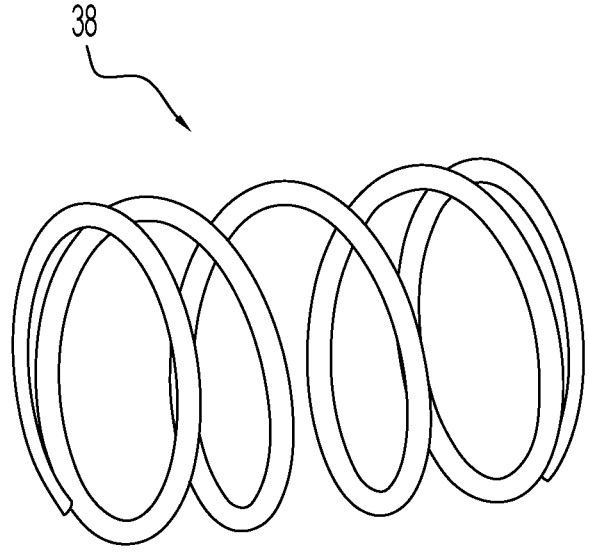
FIG. 13 is a perspective view of a biasing member of the power adapter of FIG. 1.
Figure 14:
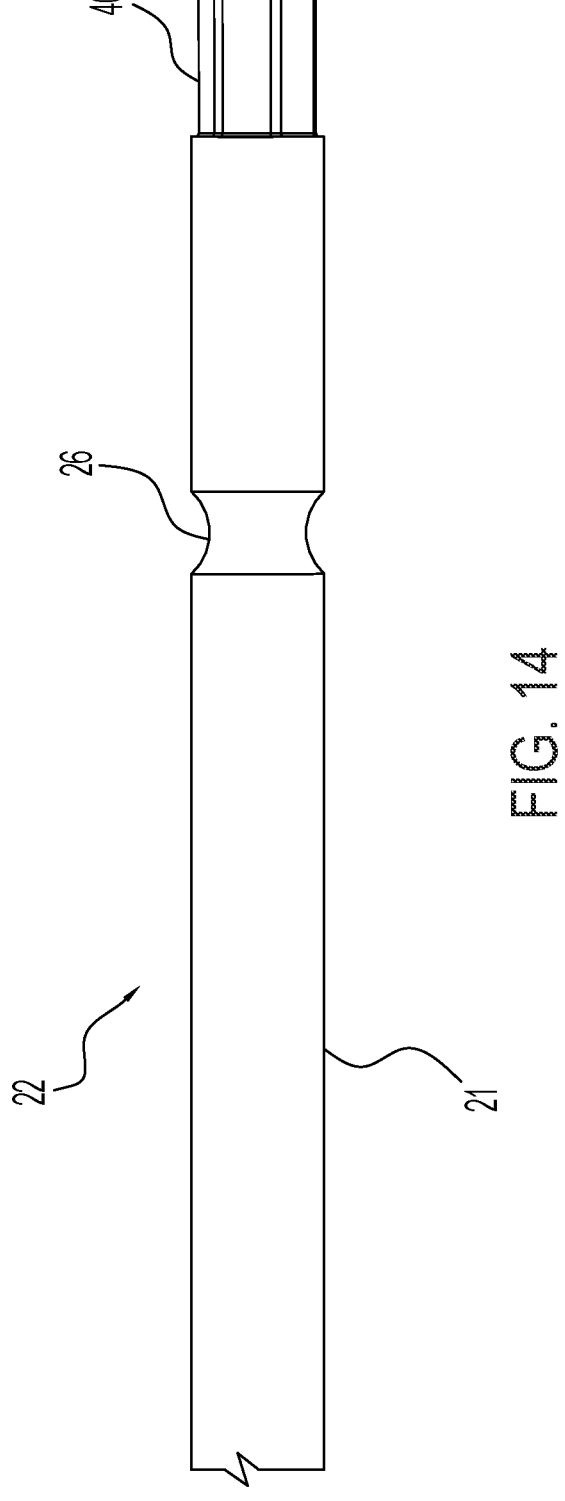
FIG. 14 is a partial perspective view of a working tool configured to be coupled to the power adapter of FIG. 1.

As best shown on FIG. 11, the dowel pin 28 is generally cylindrical and has a length which extends through the slot 30 and a diameter which allows the dowel pin 28 to move within the slot 30 between the first and second positions. In some examples, the dowel pin 28 is comprised of stainless steel, however various other materials are contemplated to be within the scope of the subject disclosure.

The locking mechanism 24 also includes a bushing 36 disposed between the sliding grip 32 and the adapter shaft 12. In some examples, the bushing 36 is disposed between the inner surface of the grip member and an outer surface of the second end 20 of the adapter shaft 12. More specifically, the bushing 36 is disposed adjacent the slot 30 about the bored cylinder of the second end 20 of the adapter shaft 12, however, other configurations are contemplated to be within the scope of the subject disclosure. Additionally, in some examples, the bushing 36 is annular (see FIG. 12) and circumscribes the adapter shaft 12. Moreover, as best shown in FIGS. 5-7, the bushing 36 is operably coupled between the biasing member 38 and the dowel pin 28. Additionally, the bushing 36 is slidable along the adapter shaft 12 as a result of movement of the sliding grip 32 and its annular abutment 34 between a distal position and a proximal position. In the distal position, the bushing 36 holds the dowel pin 28 in the first position in the slot 30 whereby the dowel pin engages the working tool 22. In the proximal position, the bushing 36 is located further from the distal end of the second end 20 of the adapter shaft 12 such that the dowel pin 28 is disposed in the second position and configured to disengage the working tool 22. More specifically, when the bushing 36 is in the proximal position, the dowel pin 28 is able to freely move proximally in slot 30 towards a second or proximal position out of engagement with the working tool 22.

The locking mechanism 24 further includes the biasing member 38. The biasing member 38 is disposed about the adapter shaft 12 and configured to bias the bushing 36 into contact with the dowel pin 28, and thereby bias the dowel pin distally towards the second end of the adapter shaft. In some examples, such as the example shown in FIGS. 3 and 4, the biasing member 38 is disposed about the bored cylinder of the second end 20 of the adapter shaft 12. However, various other configurations are contemplated to be within the scope of the subject disclosure. Moreover, the biasing member 38 is configured to bias the bushing 36 into its distal position. In this configuration, the dowel pin 28 is also biased into its first position, corresponding with the bushing 36 being in its distal position. However, other configurations are contemplated to be within the scope of the subject disclosure. The biasing member 38 may be any type of biasing member 38 including but not limited to a compression spring, an extension spring, or a torsion spring.

In operation, the user will couple the first end 14 of the adapter shaft 12 of the power adapter 10 with the rotary tool 18 such as a powered drill, a powered saw, or a powered reamer using a Hudson or chuck coupling. Then, the user will insert the shaft 21 of the working tool 22 into the counterbore 42 defined in the second end 20 of the adapter shaft 12. The force of the user inserting the shaft 21 causes the shaft 21 to push the dowel pin 28 upwardly along the slot 30 of the adapter shaft 12 against the bias of the biasing member 38 to permit further passage of the shaft 21. The shaft 21 is moved in a proximal direction until the annular groove 26 comes into alignment with the lower end of the angled slot 30, at which time the biasing member 38 urges the bushing 36 and the movable dowel pin toward the distal end of the grip member 32 until the movable dowel pin comes to rest in its first position within the annular groove 26 of the working tool 22, as shown in FIGS. 5 and 6. With the movable dowel pin 28 received or seated within the annular groove 26 under the influence of the biasing member 38, the working tool 22 is effectively locked in position within the adapter shaft 12.

When it is desired to release the working tool 22 from the second end of the adapter shaft 12, the user grasps the sliding grip 32 and pulls it from its distal position (FIGS. 5 and 6) to the proximal position (FIG. 7). In so doing, the radially inwardly directed annular abutment 34 moves from its distal position abutting the sliding collar 72 which moves the bushing 36 proximally against the bias of the biasing member 38. Concurrently, the dowel pin 28 is free to move proximally and upwardly along the angled slot 30 as shown in FIG. 7 whereby the dowel pin is released from engagement with the annular groove 26 of the working tool 22, thereby permitting the working tool 22 to be released from the adapter shaft 12. Once the working tool 22 is removed from the adapter shaft 12, a new working tool may be coupled to the power adapter 10 providing a versatile adapter which saves users the cost and time of using multiple instruments.

It will be appreciated by those skilled in the art that changes could be made to the various aspects described above without departing from the broad inventive concept thereof. It is to be understood, therefore, that the subject application is not limited to the particular aspects disclosed, but it is intended to cover modifications within the spirit and scope of the subject application as defined by the appended claims.

I claim:

1. A power adapter comprising:
   an adapter shaft having a first end for coupling to a rotary tool and a second end configured to be coupled to a working tool, wherein the second end includes a slot;
   a sliding grip housing the adapter shaft, the sliding grip including an annular abutment and a counterbore at a distal end of the sliding grip that terminates at the annular abutment; and
   a locking mechanism operatively coupled to the second end of the adapter shaft, the locking mechanism including:
      a dowel pin movable between a working tool engaging first position and a working tool releasing second position within the slot, and
      a bushing disposed between the sliding grip and the adapter shaft and movable relative to the sliding grip and the adapter shaft,
   wherein the sliding grip is movable between a distal position enabling the dowel pin to assume the first position, and a proximal position enabling the dowel pin to assume the second position.

2. The power adapter of claim 1, wherein the slot includes a longitudinal axis angled relative to a longitudinal axis of the adapter shaft.

3. The power adapter of claim 1, wherein the adapter shaft includes a counterbore about its second end coaxial with a longitudinal axis of the adapter shaft.

4. The power adapter of claim 1, wherein the adapter shaft includes a counterbore about its second end and wherein the slot is in fluid communication with the counterbore.

5. The power adapter of claim 1, wherein the sliding grip is movable relative to the adapter shaft.

6. The power adapter of claim 1, wherein the locking mechanism further comprises a biasing member biasing the bushing into contact with the dowel pin.

7. The power adapter of claim 1, wherein the locking mechanism further comprises a biasing member biasing the dowel pin distally towards the second end of the adapter shaft.

8. The power adapter of claim 1, wherein the annular abutment is configured to engage the bushing.

9. The power adapter of claim 1, wherein the annular abutment is adjacent the slot of the adapter shaft.

10. The power adapter of claim 1, wherein the first end is configured as a quick connection.

11. A powered surgical tool comprising:

a rotary tool;

the power adapter of claim 1 coupled to the rotary tool; and a working tool coupled to the power adapter.

12. The powered surgical tool of claim 11, wherein the working tool includes a connection end for coupling to the power adapter, wherein the connection end includes a groove for releasably receiving the dowel pin.

13. A power adapter comprising:

an adapter shaft having a first end for coupling to a rotary tool and a second end configured to be coupled to a working tool, wherein the second end includes a slot having a longitudinal axis angled relative to a longitudinal axis of the adapter shaft; wherein the adapter shaft further includes a counterbore about its second end and wherein the slot is in fluid communication with the counterbore;

a locking mechanism operatively coupled to the second end of the adapter shaft, the locking mechanism including:

a dowel pin movable between a working tool engaging first position and a working tool releasing second position within the slot;

a sliding grip configured to house the adapter shaft, the sliding grip including an annular abutment and a counterbore at a distal end of the sliding grip that terminates at the annular abutment, wherein the sliding grip is movable between a distal position enabling the dowel pin to assume the first position, and a proximal position enabling the dowel pin to assume the second position; and a bushing disposed between the sliding grip and the adapter shaft and movable relative to the sliding grip and the adapter shaft.

* * * * *